United States Patent
Jörimann et al.

(10) Patent No.: US 6,913,383 B2
(45) Date of Patent: Jul. 5, 2005

(54) METHOD AND APPARATUS FOR THERMALLY INVESTIGATING A MATERIAL

(75) Inventors: Urs Jörimann, Bertschikon (CH); Thomas Hütter, Niederrohrdorf (CH)

(73) Assignee: Mettler-Toledo GmbH, Greifensee (CH)

( * ) Notice: Subject to any disclaimer, the term of this patent is extended or adjusted under 35 U.S.C. 154(b) by 0 days.

(21) Appl. No.: 10/459,112

(22) Filed: Jun. 9, 2003

(65) Prior Publication Data

US 2004/0001524 A1 Jan. 1, 2004

(30) Foreign Application Priority Data

Jun. 10, 2002 (EP) .............................. 02012839

(51) Int. Cl.[7] .................. G01K 17/00; G01N 25/00
(52) U.S. Cl. ...................... 374/31; 374/102; 374/10
(58) Field of Search ................ 374/10–12, 25, 374/31, 32–33, 29, 43–44, 101–102, 4–5

(56) References Cited

U.S. PATENT DOCUMENTS

| | | | |
|---|---|---|---|
| 4,166,385 A | * | 9/1979 | Pate et al. .................. 374/31 |
| 5,152,607 A | | 10/1992 | Ibar |
| 5,174,655 A | * | 12/1992 | Litz et al. .................. 374/31 |
| 5,474,385 A | * | 12/1995 | Reading .................... 374/11 |
| 5,599,104 A | * | 2/1997 | Nakamura et al. ........... 374/12 |
| 6,170,984 B1 | | 1/2001 | Schawe et al. |
| 6,336,741 B1 | * | 1/2002 | Blaine ....................... 374/14 |
| 6,491,425 B1 | * | 12/2002 | Hammiche et al. ......... 374/43 |
| 6,551,835 B1 | * | 4/2003 | Schawe et al. ............ 436/147 |
| 6,561,692 B2 | * | 5/2003 | Danley ...................... 374/29 |
| 6,583,391 B2 | * | 6/2003 | Jorimann et al. .......... 219/497 |
| 6,641,300 B1 | * | 11/2003 | Lacey et al. ............... 374/31 |
| 6,648,504 B2 | * | 11/2003 | Danley ...................... 374/43 |
| 6,764,215 B2 | * | 7/2004 | Meyler et al. .............. 374/32 |
| 2002/0021740 A1 | * | 2/2002 | Danley ...................... 374/10 |

FOREIGN PATENT DOCUMENTS

| | | |
|---|---|---|
| EP | 0559362 | 9/1993 |
| EP | 0645619 | 3/1995 |
| EP | 1132733 | 9/2001 |
| EP | 1182439 | 2/2002 |

* cited by examiner

*Primary Examiner*—Gail Verbitsky
(74) *Attorney, Agent, or Firm*—Friedrich Kueffner (57) ABSTRACT

A method and apparatus for thermally investigating a material by driving the material through a temperature profile composed of isothermal and non-isothermal segments is disclosed, which enable determination of a kinetic component in a measured heat flow signal caused by the exposure of the material to the temperature profile.

18 Claims, 4 Drawing Sheets

METHOD AND APPARATUS FOR THERMALLY INVESTIGATING A MATERIAL

BACKGROUND OF THE INVENTION

1. Field of the Invention

The present invention relates to a method for thermally investigating a material, wherein the material is exposed to a time controlled temperature profile, and a signal representative of a resulting thermal response is measured and evaluated, said temperature profile including a succession in time of dynamic segments wherein said temperature is varied for an associated period of time, and of non-dynamic segments wherein a variation of said temperature is small in relation to said temperature variation in said dynamic segments for an associated period of time, each of said dynamic segments being interposed between two successive ones of said non-dynamic segments, said evaluation including the use of response signal values measured during time periods associated with said dynamic segments to derive a heat capacity related information from said measured response signal.

2. Description of the Related Art

A known method of this type (S. C. Mraw and D. F. Naas, J. Chem. Thermodynamics 1979, 11, 567–584) is differential scanning calorimetry (DSC), wherein the response signal is indicative of a differential heat flow which is determined as the difference between heat flows associated with a sample material and a reference material. In this known method, all time periods associated with the non-dynamic segments are of uniform length. Similarly, the time periods associated with the dynamic segments are of uniform length, and the temperature variation is linear at the same constant rate in all dynamic or non-isothermal segments. A hypothetical isothermal baseline is calculated for each non-isothermal segment as a linear interpolation of the differential heat flow signal measured during the periods associated with the two isothermal segments which have the respective non-isothermal segment interposed therebetween. This hypothetical baseline is subtracted from the heat flow signal measured during the period of the non-isothermal segment, and the heat capacity of the material is calculated from this difference.

Another known method (H. Staub and W. Perron, Analytical Chemistry, Vol. 46, No. 1, January 1974, pp. 128–130) uses a temperature profile composed of isothermal temperature steps. The temperature difference between successive isothermal segments was decreased as the temperature was increased. Further, the length of the time period associated with the isothermal step segments was increased with increasing temperature. The peak areas defined by the heat flow signal caused in each step was used to calculate the melting enthalpy of the material in order to therefrom derive an impurity fraction of the material.

Another known method (EP 0 559 362 A1) uses a temperature profile which is a superposition of a linear temperature ramp and a periodic temperature modulation function having a predetermined modulation amplitude and frequency. Two signal components are derived from the resulting periodic heat flow signal, one of these components being related to the heat capacity of the investigated material. In this method, changes in the baseline and a resulting influence on the evaluation of the heat flow signal remain undetected.

SUMMARY OF THE INVENTION

It is an object of the present invention to provide a method of the above referenced type which yields enhanced information about the investigated material. It is a further object of the invention to provide an apparatus for performing this method.

In order to attain these objects, the method according to the present invention is characterized in that response signal values measured during time periods associated with non-dynamic segments are used to derive a kinetic component of said measured response signal.

In the method of the invention, the temperature profile or temperature program is controlled while the temperature of the exposed material to be investigated passively follows the temperature profile. When applying the method to the important case of differential scanning calorimetry, where the resulting response signal is differential heat flow measured between the material to be investigated, i. e. the sample material, and a thermally inert reference material, the response signal associated with the dynamic segments may be seen in relation to the one obtained in ordinary differential scanning calorimetry (DSC), where the temperature is linearly varied over a period of time between an initial value and a final value and the measured heat flow is related to the heat capacity of the investigated material. In contrast, the resulting heat flow signal associated with the non-dynamic segments, which are isothermal or have a sufficiently small temperature variation as compared to the dynamic segments, apart from including a contribution caused by an undesired isothermal drift will include heat flow contributions from kinetic events which occur in the material under investigation. These kinetic contributions are normally much larger than the contributions caused by the isothermal drift, and it is for many applications sufficient to directly use the signal values associated with the non-dynamic segments as a representation for the kinetic component of the resulting heat flow signal. The kinetic component allows to investigate particulars of a chemical reaction which occurs in the material. Similar considerations apply to the example of power compensation calorimetry, where the resulting response signal is indicative of a heating power applied to the material. It is evident that the method of the present invention is also applicable to Differential Thermal Analysis (DTA), where a temperature difference between the sample material and a reference material is measured as the resulting thermal response. This may also be modified to only measure the sample temperature and replace the reference material by a calculational model for obtaining the temperature difference (SDTA). In all cases the method of the invention allows to optimize or shorten the duration of experimental runs and at the same time provides for simultaneous determination of the specific heat $c_p$ and of a kinetic component.

It is expedient to embody the invention so that in each associated time period said response signal values used to derive a kinetic component are selected among those measured at times later than a time distance from the start of each associated time period, said time distance being selected so as to essentially reduce transitional effects from transitions between successive dynamic and non-dynamic segments. A practical apparatus for performing the method always involves a time constant. This has the consequence that there is always a transitory period which is necessary for the temperature to assume its intended value, in particular a constant isothermal value, at the transition from a dynamic, non-isothermal segment to a subsequent non-dynamic segment. By selecting only those signal values for the derivation of the kinetic component which are at a sufficient time distance from the start of the non-dynamic section, these transitional effects may be excluded or at least essentially reduced in the evaluation. As an example, the kinetic component may be derived by selecting one value in each isothermal segment which is at 75% of the associated time period.

For the same practical reason of a time constant, it is appropriate to embody the invention so that in each associated time period said signal values used to derive a heat capacity related information are selected among those measured at times later than a time distance from the start of each associated time period, said time distance being selected so as to essentially reduce transitional effects from transitions between successive non-dynamic and dynamic segments. The time constant similar to the above causes a transitory period to occur until the desired temperature variation of the dynamic segments has been stably established after the end of the respective leading non-dynamic segments. Selecting the signal values used for the heat capacity related information at a sufficient distance from the end of the leading non-dynamic segment, which is the start of the successive dynamic segment, allows to exclude or at least essentially reduce these transitional effects from the evaluation.

In a practical embodiment it is provided that said measured values used to derive said kinetic component and/or said heat capacity related information are interpolated so as to produce an essentially continuous curve representation for said kinetic component and/or heat capacity related information. Specifically, these continuous curve representations are well suited for visual display.

According to a preferred aspect of the invention, the method is characterized in that a reference material is exposed to said temperature profile and a signal representative of the difference between the thermal responses associated with the material to be investigated and the reference material is determined and used as said signal representative of a resulting thermal response. The invention is thereby implemented as what is well known in the art as a "differential" method, e. g. differential scanning calorimetry or power compensation calorimetry. In such methods, the material to be investigated and a reference material, which is usually inert and well known, are simultaneously exposed to the same temperature profile, and the signal which is evaluated corresponds to the difference between thermal responses, e. g. the heat flows associated with the two materials or the difference in heating powers for causing a temperature difference between the two materials to approach zero. The need for an absolute measurement of the response, e. g. an absolute heat flow or heating power measurement, is not necessary, since it is sufficient to measure the difference and the accuracy of the measurement accordingly increased. Alternatively, the individual responses of the material to be investigated and the reference material may be measured and then suitably processed and combined to yield the difference of thermal responses.

Within the scope of the invention it is further provided that a signal representative of a thermal response associated with said non-dynamic segments when no material is exposed to said temperature profile is measured and used to define a baseline signal which is subtracted from said signal representative of a resulting thermal response when material is exposed to said temperature profile to thereby form a baseline corrected signal, said evaluation making use of said baseline corrected signal. In any practical apparatus for performing the method of the invention, a non-zero thermal response signal occurs during the non-dynamic segments even when no material is exposed to the temperature profile, and this non-zero response signal is dependent on time. This signal is due to thermal asymmetries and isothermal drift of the practical apparatuses used to perform the method. While this baseline signal relies on signal values measured during the time periods of the non-dynamic segments, preferably excluding the initial transitory portions of these periods, a baseline which may be utilized for the whole temperature profile including the time periods associated with the dynamic segments may be obtained by suitable interpolation. Using the baseline corrected signal for the evaluation advantageously results in a compensation of the final results for thermal asymmetry and isothermal drift of the apparatus used to perform the method.

As an example for the evaluation of the heat capacity related information in heat flow calorimetry utilizing the baseline correction, use can be made of the following relation between the heat flow dH/dt and the specific heat cp $$\frac{dH}{dt} = k * cp * m * \frac{dT}{dt} \qquad (1)$$

wherein m is the mass of the material under investigation, T is the temperature value of the temperature profile and k is a calibration factor for the apparatus used to perform the method.

Similar to conventional differential scanning calorimetry (DSC), a constant heating rate $dT/dt=\beta$ may be used for the temperature variation during the dynamic segments. With this constant heating rate, a well known material like sapphire may be driven through the temperature profile. The baseline signal obtained in an empty run through the temperature profile is subtracted from the heat flow which was measured for the sapphire material to thereby derive the baseline corrected heat flow $dH_{sapphire\_corr}/dt$. With the constant heating rate $\beta$, equation (1) then takes the form $$dH_{sapphire\_corr}/dt = k * cp_{sapphire} * m_{sapphire} * \beta \qquad (2)$$

Using literature values for $cp_{sapphire}$ as a function of temperature T allows to determine the calibration factor k from equation (2) as $$k = dH_{sapphire\_corr}/dt * 1/(cp_{sapphire} * m_{sapphire} * \beta) \qquad (3)$$

The same run with the sample material to be investigated and after again applying the baseline correction yields the baseline corrected heat flow $dH_{sample\_corr}/dt$ for the sample material similar to equation (2)

$$dH_{sample\_corr}/dt = cp_{sample} * m_{sample} * \beta * k \qquad (4)$$

With the calibration factor k known from equation (3), the specific heat $cp_{sample}$ of the sample material is then given as $$cp_{sample} = dH_{sample\_corr}/dt * 1/(m_{sample} * \beta * k) \qquad (5)$$

$$= dH_{sample\_corr}/dt / dH_{sapphire\_corr}/dt *$$

$$cp_{sapphire} * m_{sapphire}/m_{sample}$$

Within the framework of the present invention, various forms of temperature profiles may be used.

In one embodiment, the time periods associated with the non-dynamic segments are of varying length. This is specifically useful to optimize the time duration which is required for a complete run considering the fact that the transitory periods which occur at a change from a non-dynamic segment to a dynamic segment and vice versa depend on temperature. In this case, the lengths of the time periods associated with the isothermal segments vary as a function of a quantity which is determined by the temperature. For example, this quantity may be the instantaneous value of the temperature, or the first or higher derivatives of temperature with respect to time. It has been found that this temperature dependency is normally so that the transitory period decreases with increasing temperature.

In another embodiment, the lengths of time periods associated with the non-dynamic segments vary as a function of a quantity which is determined by the response signal, for example the heat flow. For example, this quantity may be the instantaneous value of the response signal or the first or higher derivatives of the response signal with respect to time. This is specifically useful to accommodate to the transitory behavior of the material which is exposed to the temperature profile and allows to optimize the overall time which is needed to perform the measurement.

In another alternative it is provided that the temperature values of the non-dynamic segments vary as a function of a quantity which is determined by the response signal, for example the heat flow. Thereby the temperature steps between the temperatures associated with successive non-dynamic segments depend on the response of the material which is exposed to the temperature profile. For instance, if the response, e. g. a measured heat flow signal, starts to vary appreciably, the magnitude of the temperature steps may be decreased thereby attaining a better temperature resolution of the response.

In a still further embodiment it is provided that the rate of variation of the temperature associated with said dynamic segments is a function of a quantity which is determined by the response signal, for example the heat flow. In this case, the rate of variation of the temperature, i. e. the heating rate, is dependent on the response of the material exposed to the temperature profile. For instance, if the measured heat flow is small, the heating rate could be increased in order to obtain a higher signal value. Thereby a more accurate measurement of the specific heat may be attained.

It will be understood from the above that all combinations among the before referenced specific embodiments wherein the shape of the temperature profile depends on a quantity which is determined by the measured response, for example the instantaneous value of the response or the first or any higher derivative of the response signal with respect to time, are feasible. These combinations may ultimately result in optimum sensitivity and temperature resolution with minimum time requirements for a complete experimental run.

It will be further understood that all embodiments may be operated in an experiment where the measurement is made only under the condition that the material to be investigated is exposed to the temperature profile, while no separate measurements for determining an updated baseline or an updated calibration factor are carried out. This will yield quick information about a relative separation between the heat capacity related information and the kinetic component in the measured thermal response. However, a determination of specific heat with high accuracy is in this case not possible.

Alternatively, operating the method in a way that an updated baseline is determined in a measurement with no material exposed to the temperature profile in addition to the measurement performed with the material exposed allows an absolute separation between the heat capacity related information and the kinetic component. The accuracy of the derived heat capacity depends, however, on the quality of adjustment of the thermal response, specifically of heat flow adjustment.

In order to attain an absolute separation of the heat capacity related information and the kinetic component and for determining the heat capacity with very high accuracy, a measurement for an updated calibration factor should be performed with a suitable material, e. g. sapphire, exposed to the temperature profile in addition to the measurements for the updated baseline with no material exposed and the actual measurement for the material exposed to the temperature profile.

It should also be noted that in the above measurements the identical temperature profile should be used for the material to be investigated and the determinations of the baseline and/or the calibration factor, if any. As a consequence, if the temperature profile is so as to depend on the measured heat flow signal, as is the case in some of the before-referenced embodiments, the measurement with the material to be investigated exposed should be carried out first to thereby identify the temperature profile, while the measurements for determining the baseline and/or the calibration factor have subsequently to be performed with this temperature profile.

The method in accordance with the invention may be performed with a conventional differential scanning calorimeter or with a conventional power compensation calorimeter modified to be controlled in accordance with an appropriate heating program and performing an evaluation of the measured heat flow signal or differential power signal, respectively, in accordance with the claimed method.

Further, it is to be understood that in the context of the present specification the terms "heat flow", "source of thermal energy" and related terms are intended to mean either heating or cooling. In the latter case, the "source of thermal energy" will e. g. be a source of a cooling agent thermally coupled to the material under investigation.

BRIEF DESCRIPTION OF THE DRAWING

In the following description, the method for thermally analyzing a material in accordance with the invention is exemplarily explained in conjunction with an apparatus adapted for performing the method with reference to the accompanying drawings, in which.

DETAILED DESCRIPTION OF THE PREFERRED EMBODIMENTS

Figure 1:
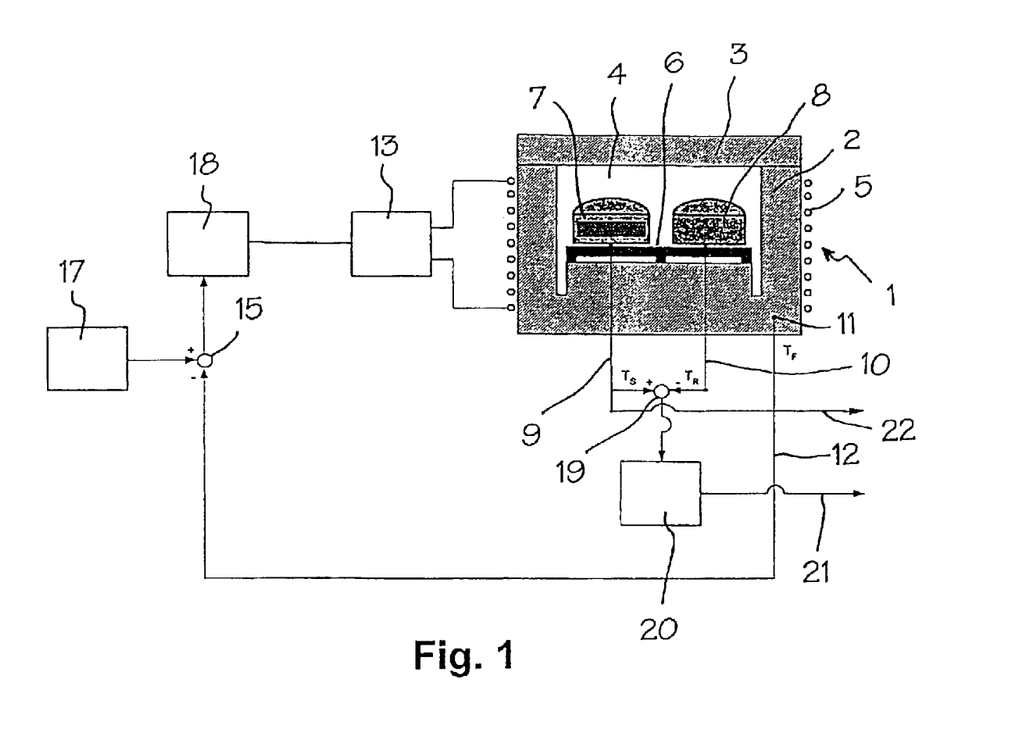
FIG. 1 is a schematic diagram of an embodiment of an apparatus for thermally analyzing a material.

FIG. 1 schematically illustrates a source of thermal energy formed by a heat source 1 having an essentially hollow cylindrical oven block 2 made of silver. The upper face of oven block 2 is formed as a removable lid 3 for opening and closing block 2 to permit access to the interior 4 thereof. A winding of heating wire 5 is wound onto the exterior cylindrical surface of oven block 2 to provide for resistive heating. Alternatively, a flat resistive heater could be applied to the lower face of oven block 2 opposite to lid 3 or any other suitable portion of oven block 2.

A disc-shaped substrate 6 is arranged in the interior of oven block 2 in thermal contact therewith. Substrate 6 has two circular areas thereof formed as a sample holder and a reference holder, respectively, adapted to support a sample pan 7 in a sample position and a reference pan 8 in a reference position, respectively, in a thermally symmetrical manner. Each of the circular areas of the sample and reference holders are formed with a thermocouple arrangement for detecting the temperatures $T_S$ and $T_R$ of the sample and reference pans 7, 8, respectively. In the illustration of FIG. 1, the electrical signals representing the sample and reference temperatures $T_S$ and $T_R$, respectively, are fed to the outside of heat source 1 by means of signal lines 9 and 10, respectively, for connection to the input side of a subtractor 19 which produces a signal representative of difference between the sample and reference temperatures $T_S$ and $T_R$. In practice, the thermocouple arrangement may, however, be connected so as to simply feed out an electrical signal representative of the temperature difference between $T_S$ and $T_R$. The reference pan 8, alternatively empty or accommodating an inert material, serves as a reference material for the measurement, as is well known in the art of differential scanning calorimetry.

A platinum thermometer 11 arranged at the bottom portion of oven block 2 detects a temperature $T_F$ of oven block 2, and a corresponding electrical signal is fed to the outside by signal line 12. Electrical heating power is supplied to heater winding 5 of heat source 1 by a power amplifier 13.

The signal on signal line 12 representing the measured temperature $T_F$ of heat source 1 is applied to one input of a subtractor 15. The other input terminal of subtractor 15 is connected to the output of a temperature programmer 17. Temperature programmer 17 outputs a control signal which represents a temperature-versus-time function defining a temperature profile for heat source 1. The output signal of subtractor 15 being representative of the difference between the control signal from temperature programmer 17 and the temperature signal $T_F$ on signal line 12 is applied to a control input of a temperature controller 18 which generates a corresponding control signal for power amplifier 13. As a result, the control loop formed by signal line 12, temperature programmer 17, subtractor 15, temperature controller 18 and power amplifier 13 drives the heater winding 5 so that the heat source 1 follows the temperature-versus-time function commanded by temperature programmer 17.

It is well known in calorimetry that heat flow along a heat flow path is proportional to a difference between temperatures measured at arbitrarily selected locations which are spaced apart along the path. In particular, the heat flow between the sample position and the heat source 1 is proportional to a difference between the sample temperature $T_S$ and the heat source temperature $T_F$. Similarly, the heat flow between the reference position and the heat source 1 is proportional to a difference between the reference temperature $T_R$ and the heat source temperature $T_F$. For complete thermal symmetry between the sample and reference positions a differential method conventionally assumes a differential heat flow to be proportional to the difference between sample and reference temperatures $T_S$ and $T_R$, respectively. Based on this, the signal representing the difference between $T_S$ and $T_R$ is applied to a heat flow calculation unit 20, and the calculated heat flow and the measured sample temperature $T_S$ are fed to an evaluation unit (not shown) on signal lines 21 and 22, respectively, for further processing. Alternatively, the measured reference temperature $T_R$ could be fed to the evaluation unit instead of or in addition to the measured sample temperature $T_S$. The further processing includes the evaluation of a functional relation between heat flow and any of the temperatures $T_S$, $T_R$ or $T_F$. Those of ordinary skill will also understand that, instead of $T_S$, $T_R$ and $T_F$, temperature measurements at other suitable locations in the heat flow paths between the heat source 1 and the sample and reference positions could be used to determine the resulting heat flow.

The temperature profile of the heat source 1 as commanded by the temperature programmer 17 and controlled by the temperature controller 18 generally includes an alternating sequence of non-dynamic isothermal and dynamic non-isothermal segments wherein the period of time associated with each isothermal or non-isothermal segment may generally vary from segment to segment. Further, the temperature steps between successive isothermal segments may vary, as may the shape of the non-isothermal segments which extend between successive ones of the isothermal segments.

Figure 2:
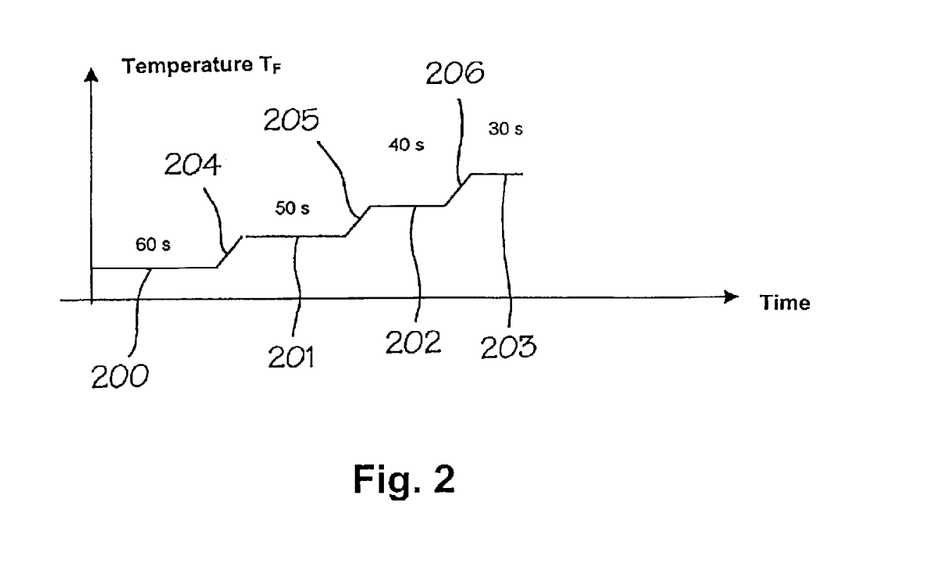
FIG. 2 is a schematic diagram illustrating a first example of a temperature profile used in performing the method.

A simple practical example for the temperature profile is illustrated in FIG. 2, where the temperature $T_F$ of the heat source 1 is plotted as a function of time. The length of the time period associated with the initial isothermal segment 200 of the temperature profile is 60 seconds. Each of the successive isothermal segments 201, 202, 203 is shorter than the respective preceding one by a decrement of 10 seconds resulting in durations of 50, 40 and 30 seconds, respectively. The temperature step, i. e. the temperature difference between successive isothermal segments, has a constant value of $\Delta T$. The principle behind this example is a temperature profile wherein the temperature of the isothermal segments increases with time at constant temperature increments while the duration of the isothermal segments decreases with time at constant time decrements. In the specific example of FIG. 2 it is assumed that the temperature variation during the non-isothermal segments 204, 205 and 206 is linear at a constant rate while the periods of time associated with the non-isothermal segments have the same length.

Figure 3:
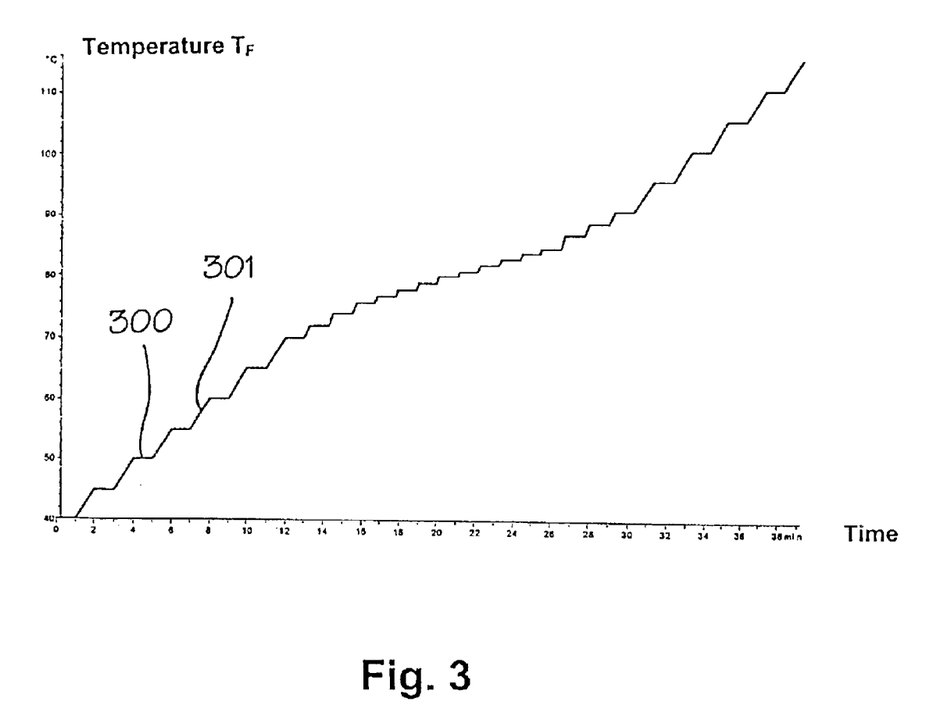
FIG. 3 is a schematic diagram illustrating a second example of a temperature profile used in performing the method.

FIG. 3 is illustrative for a more advanced temperature profile. In this temperature profile, the length of the time periods associated with the isothermal segments 300 and the non-isothermal segments 301 are variable. The temperature increments between successive isothermal segments (or decrements in case of cooling) vary as well. The rate of temperature variation during the non-isothermal segments is also variable. These variations may depend on the temperature and/or the measured heat flow or on quantities which are derived therefrom. As an example, these variations may depend on the instantaneous values of temperature and/or heat flow and/or on the first and/or higher derivatives with respect to time of the temperature and/or heat flow curves. In these cases, the simplified illustration of FIG. 1 has to be enhanced to include at least some feedback of the temperature and/or the measured heat flow on line 21 or quantities that are derived therefrom to the temperature programmer 17 to enable the latter one to program a desired dependency between the shape and duration of the isothermal and non-isothermal segments and the actual temperature and/or heat flow. Such enhancement is illustrated in FIG. 5 where the same reference numerals are used for those elements already incorporated in the embodiment of FIG. 1. The embodiment of FIG. 4 in addition includes a feedback loop 401 for the heat flow signal on line 21. The feedback loop 401 comprises a temperature program modifier 402. Temperature program modifier 402 receives the feedback heat flow signal and in response thereto produces an output signal to temperature programmer 17 which causes the temperature programmer 17 to modify the control signal for the temperature profile of heat source 1 in accordance with the desired variations. Reasonable orders of magnitude for the length of the time periods of the isothermal and non-isothermal segments are tens of seconds to minutes, for the rate of temperature change during the non-isothermal segments are 1 K/minute, and for the temperature steps between successive isothermal segments are 1 to 10 K.

Figure 4:
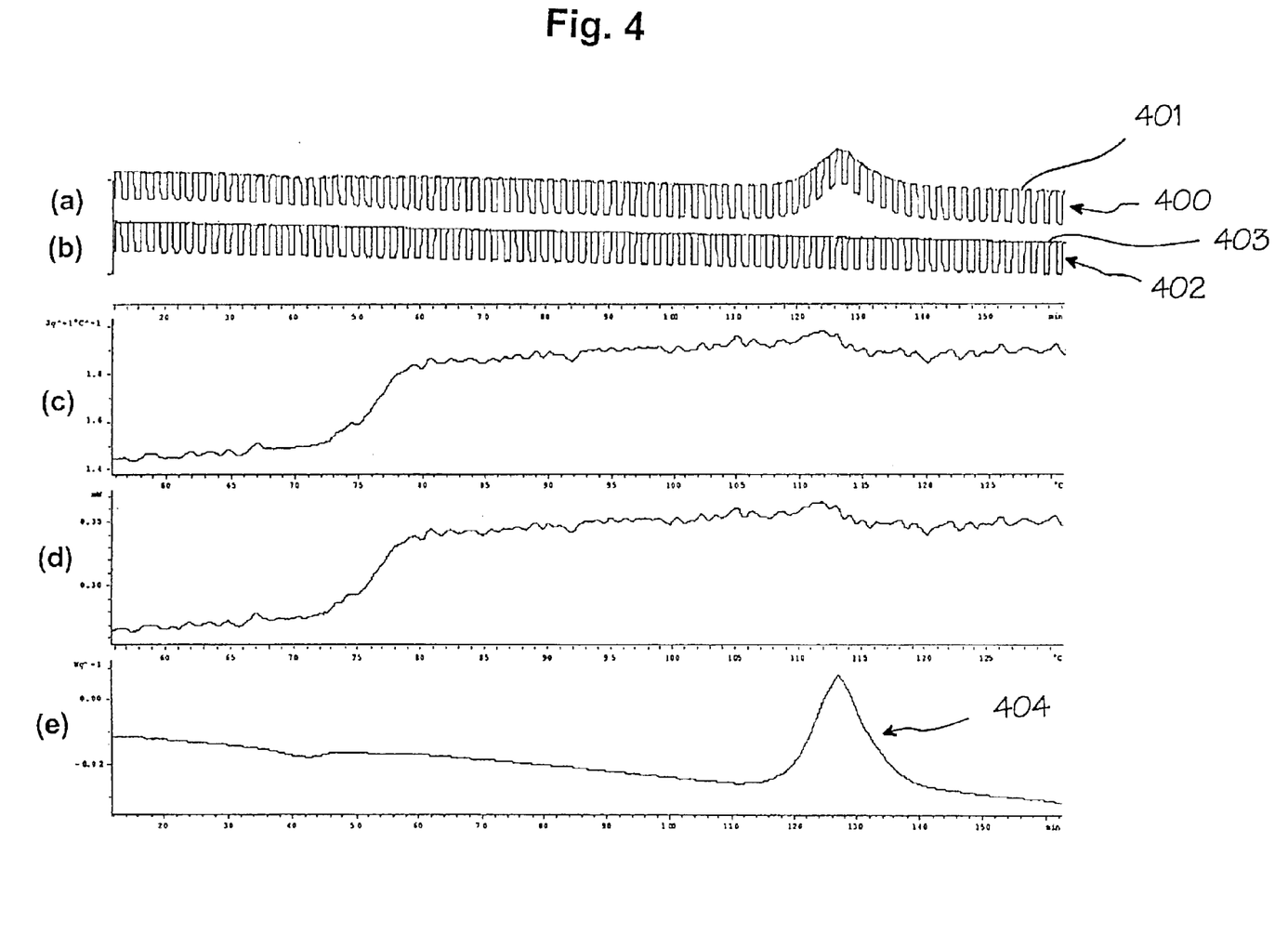
FIG. 4 is a schematic diagram exemplarily illustrating a result of the evaluation of heat flow resulting from the method in accordance with the invention.
Figure 5:
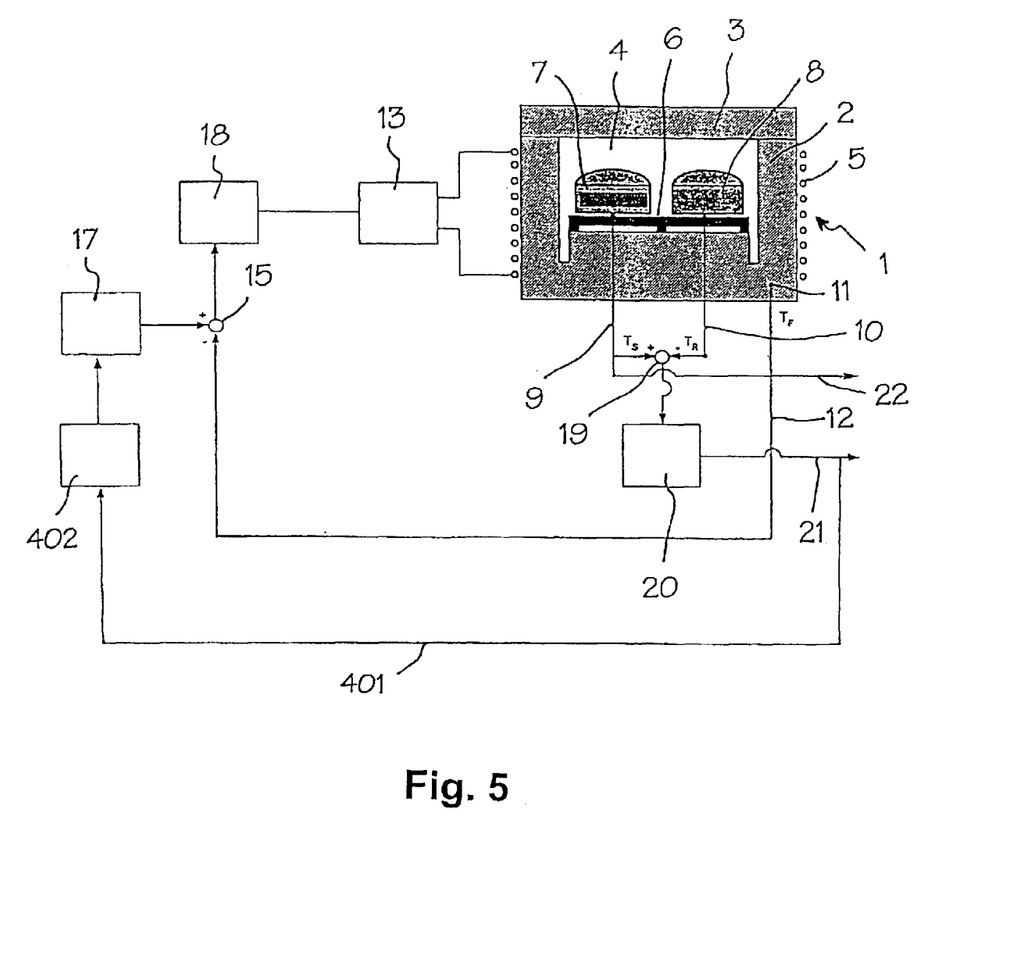
FIG. 5 is a schematic diagram of a modification of the embodiment of FIG. 1.

FIG. 4 exemplarily illustrates the evaluation of the measured heat flow signal using a temperature profile of the general type exemplified in FIGS. 2 or 3. The evaluation is based on equations 1 to 5 which have been set out earlier in this specification.

FIG. 4(a) shows the heat flow signal 400 measured with the sample material exposed to the temperature profile. It also shows the baseline 401 which is obtained by interpolation of the heat flow signal measured during the isothermal segments during those portions of the associated time periods wherein transitory effects from the transitions between non-isothermal and isothermal segments have already come down.

FIG. 4(b) shows the same for the inert material exposed to the same temperature profile. Reference numeral 402 designates the corresponding measured heat flow signal while reference numeral 403 indicates the interpolated baseline.

FIG. 4(c) shows the heat capacity of the sample material calculated in accordance with equation (5) from the heat flow values measured during the non-isothermal segments of the temperature profile and excluding those portions of the associated time periods where transitory effects from the transitions between isothermal and non-isothermal segments have not yet sufficiently settled.

FIG. 4(d) illustrates a calculated heat flow component which is obtained by multiplying the heat capacity values from FIG. 4(c) with the average heating rate during the non-isothermal segment and the mass of the sample.

FIG. 4(e) illustrates the kinetic component 404 of the measured heat flow signal which is obtained as an interpolation curve of signal values measured during the isothermal segments at times where transitory effects caused by the transitions between isothermal and non-isothermal segments have settled.

Those of ordinary skill in the art will understand that the above exemplary description as has been made with reference to differential heat flow scanning calorimetry is analogously applicable to differential power compensation calorimetry. In the latter case, the main difference with respect to the embodiments illustrated in FIGS. 1 and 5 is the provision of separately controllable heaters for the sample and reference positions 7, 8 in FIGS. 1 and 5. Control of these heaters is such that the average of the sample and reference holder temperatures $T_S$ and $T_R$ follows the desired temperature profile while the difference between the sample and reference holder temperatures $T_S$ and $T_R$ is controlled to approach zero, as is well familiar to a person of ordinary skill in the field of calorimetry. A signal indicative of the differential power applied by the two heaters to the sample and reference positions is then used as the response signal, and is analyzed instead of the heat flow signal of heat flow differential calorimetry to thereby simultaneously derive a heat capacity related information and a kinetic component in a similar manner as has been described above for heat flow differential scanning calorimetry.

Further, a person of ordinary skill will easily understand that the invention is not limited to a differential method. In particular, the reference holder exemplarily illustrated and described with reference to FIGS. 1 and 5 need not be present, and the proportion of heat flow caused by a sample in the sample pan 7 may be determined in other ways, e. g. by using a mathematical model or by performing separate runs with the empty sample pan 7 and the sample present in sample pan 7.

What is claimed is:

1. A method for thermally investigating a material, comprising exposing the material to a time controlled temperature profile, and measuring and evaluating a thermal response signal (400) representative of a resulting thermal response, said temperature profile including a succession in time of dynamic segments (204, 205, 206; 301) wherein a temperature is varied for an associated period of time, and of non-dynamic segments (200, 201, 202, 203; 300) wherein a variation of said temperature is small in relation to a temperature variation in said dynamic segments for an associated period of time, each of said dynamic segments being interposed between two successive ones of said non-dynamic segments, wherein evaluating the measured thermal response signal (400) includes the use of response signal values measured during time periods associated with said dynamic segments (204, 205, 206; 301) to derive a heat capacity related information from said measured thermal response signal, further comprising using the response signal values measured during time periods associated with non-dynamic segments (200, 201, 202, 203; 300) to derive a kinetic component (404) of said measured response signal (400).

2. A method according to claim 1, comprising selecting in each associated time period said response signal values used to derive the kinetic component (404) among those measured at times later than a time distance from the start of each associated time period, said time distance being selected so as to essentially reduce transitional effects from transitions between successive dynamic and non-dynamic segments.

3. A method according to claim 2, comprising selecting in each associated time period said response signal values used to derive a heat capacity related information among those measured at times later than the time distance from the start of each associated time period, said time distance being selected so as to essentially reduce transitional effects from transitions between successive non-dynamic and dynamic segments.

4. A method according to claim 3, comprising interpolating said response signal measured values used to derive said kinetic component and/or said heat capacity related information so as to produce an essentially continuous curve representation for said kinetic component and/or heat capacity related information.

5. A method according to claim 1, comprising exposing a reference material to said temperature profile and determining a signal representative of the difference between the measured thermal responses associated with the material to be investigated and the reference material and using said signal as said signal representative of the resulting thermal response.

6. A method according to claim 1, comprising measuring a signal representative of a thermal response associated with said non-dynamic segments when no material is exposed to said temperature profile and using said signal to define a baseline signal which is subtracted from said signal representative of a resulting thermal response when the material is exposed to said temperature profile to thereby form a baseline corrected signal, said evaluation making use of said baseline corrected signal.

7. A method according to claim 1, wherein the time periods associated with the non-dynamic segments are of varying lengths.

8. A method according to claim 7, characterized in that the lengths of the time periods associated with the non-dynamic segments vary as a function of said temperature or a quantity derived from said temperature.

9. A method according to claim 7, wherein the lengths of time periods associated with the non-dynamic segments vary as a function of the measured response signal or a quantity derived from said response signal.

10. A method according to claim 1, wherein the non-dynamic segments have temperature values, and wherein the temperature values of the non-dynamic segments vary as a function of the measured response signal or a quantity derived from said response signal.

11. A method according to claim 1, wherein a rate of variation of the temperature associated with said dynamic segments is a function of the measured response signal or a quantity derived from said response signal.

12. A method according to claim 1, wherein said measured response signal is indicative of heat flow.

13. A method according to claim 5, wherein the difference between a resulting temperature of said material to be investigated and a resulting temperature of said reference material, while said material to be investigated and said reference material are exposed to said temperature profile, is measured and used as said signal representative of the resulting thermal response.

14. A method according to claim 5, wherein, while exposing said material to be investigated and said reference material to said temperature profile, heating powers applied to each of said material to be investigated and said reference material are controlled so as to cause the difference between a resulting temperature of said material to be investigated and a resulting temperature of said reference material to approach zero, and a signal representing a resulting difference between the heating powers applied to said material to be investigated and said reference material is used as a resulting response signal.

15. A method according to claim 1, wherein at least one of said non-dynamic segments is an isothermal segment wherein said temperature is kept constant for the associated period of time.

16. An apparatus for thermally investigating a material, the apparatus comprising
a source of thermal energy (1),
a controller (18) for controlling a temperature of said source (1) in accordance with a time controlled temperature profile including a succession in time of dynamic segments (204, 205, 206; 301), wherein said temperature is varied for an associated period of time, and of non-dynamic segments (200, 201, 202, 203; 300) wherein a variation of said temperature is small in relation to a temperature variation in said dynamic segments for an associated period of time, each of said dynamic segments being interposed between successive ones of said non-dynamic segments,
a sample holder having a sample position (7) adapted to receive a sample of a material to be investigated, said sample position being thermally coupled to said source (1) for allowing heat flow therebetween,
a device for measuring temperature data indicative of said heat flow associated with said sample position, and for issuing a corresponding heat flow signal,
a processor for receiving said heat flow signal, said processor being programmed to derive a heat capacity related information from values of said heat flow signal (400) measured during time periods associated with said dynamic segments,
wherein said processor is programmed to derive a kinetic signal component (404) from values of said heat flow signal (400) measured during time periods associated with said non-dynamic segments.

17. An apparatus according to claim 16, comprising a reference holder having a reference position (8) adapted to receive a reference material, said reference position being thermally coupled to said source for allowing heat flow therebetween, said temperature data measuring device being adapted to measure temperature data associated with said sample and reference positions, and for issuing a signal representative of a difference between the heat flows associated with said sample and reference, said processor being programmed to use a difference signal to derive said heat capacity related information and said kinetic signal component.

18. An apparatus for performing the method of claim 14, comprising
a sample holder having a sample position adapted to receive a sample of a material to be investigated, said sample position being thermally coupled to a first source of thermal energy,
a reference holder having a reference position adapted to receive a reference material, said reference position being thermally coupled to a second source of thermal energy, a device for measuring a difference between a temperature at said sample position and a temperature at said reference position,
a controller for controlling heating powers of said first and second sources of thermal energy so as to cause said difference between said temperatures to approach zero, and to cause said sample and reference positions to be exposed to a time controlled temperature profile including a succession in time of dynamic segments (204, 205, 206; 301),
wherein a temperature value of said temperature profile is varied for an associated period of time and of non-dynamic segments (200, 201, 202, 203; 300) wherein a variation of said temperature value is small in relation to a temperature value variation in said dynamic segments for an associated period of time, each of said dynamic segments being interposed between successive ones of said non-dynamic segments,
a processor for receiving a signal indicative of a difference between the heating powers of said first and second sources of thermal energy, said processor being programmed to derive a heat capacity related information from values of a difference signal measured during time periods associated with said dynamic segments,
wherein said processor is programmed to derive a kinetic component from values of said difference signal measured during time periods associated with said non-dynamic segments.

* * * * *